United States Patent
Krueger et al.

(10) Patent No.: US 7,666,253 B2
(45) Date of Patent: Feb. 23, 2010

(54) TEST FIXTURE FOR COLLECTING PARTICULATE MATERIAL

(75) Inventors: Ernest M. Krueger, Devine, TX (US); Timothy L. Travis, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 658 days.

(21) Appl. No.: 11/498,675

(22) Filed: Aug. 3, 2006

(65) Prior Publication Data

US 2007/0069718 A1  Mar. 29, 2007

Related U.S. Application Data

(60) Provisional application No. 60/721,743, filed on Sep. 29, 2005.

(51) Int. Cl.
B01D 49/00 (2006.01)
(52) U.S. Cl. .............................. 96/413; 55/490; 55/495; 55/496; 73/28.01; 73/28.04; 73/28.05; 73/863.21
(58) Field of Classification Search .................. 96/413; 55/490, 495, 496; 73/28.01, 28.04, 28.05, 73/863.21
See application file for complete search history.

(56) References Cited

U.S. PATENT DOCUMENTS 2,145,683 A * 1/1939 Bostock ..................... 96/225
3,857,688 A * 12/1974 Wisnewski ................. 55/483
4,171,963 A * 10/1979 Schuler ...................... 55/302
4,836,922 A * 6/1989 Rishel et al. ............... 210/232
5,606,854 A * 3/1997 Hoffmann .................. 60/274
5,741,419 A  4/1998 Baxter
5,785,870 A * 7/1998 Davis et al. ................ 210/798
5,887,477 A  3/1999 Newman
5,916,440 A * 6/1999 Garcera et al. ............. 210/232
6,214,300 B1  4/2001 Morrison

* cited by examiner

Primary Examiner—Robert J Hill, Jr.
Assistant Examiner—Christopher P Jones
(74) Attorney, Agent, or Firm—Gunn & Lee, P.C.

(57) ABSTRACT

A test fixture for collecting particulate matter carried in the exhaust gas stream of an engine has a pair of coaxially aligned mounting plates, each having a filter cartridge holder mounted thereon. One of the mounting plates is moveable with respect to the other along a predefined longitudinal axis of the test fixture between an open position, whereat a filter cartridge is easily placed or removed, and a closed position at which a filter media mounted in the filter cartridge is sealed during a prescribed test sequence. An actuator mounted on a third coaxially aligned mounting plate has an extendable rod connected to the second mounting plate to effect movement of the second mounting plate between the open an closed positions.

6 Claims, 3 Drawing Sheets

TEST FIXTURE FOR COLLECTING PARTICULATE MATERIAL

This is a non-provisional application claiming priority to U.S. Provisional Application Ser. No. 60/721,743, filed Sep. 29, 2005.

BACKGROUND OF THE INVENTION

1. Technical Field

This invention relates generally to a test fixture for holding a filter exposed to an exhaust gas stream, and more particularly to such a test fixture for collecting particulate matter emitted from an engine during a defined test sequence.

2. Background Art

The U.S. Environmental Protection Agency (EPA) has set very stringent emissions standards for nonroad engines and heavy-duty highway vehicle engines. The standards are directed at reducing smog-causing emissions from stationary engines, off-road vehicles, trucks, buses, recreational vehicles, and motor homes. In particular, standards set forth for model year 2007 limit heavy-duty highway engine particulate matter (PM) emissions to 0.01 g/bhp-hr.

Extensive engine development, testing, and validation will be required to achieve and certify that engines manufactured in 2007, and later, meet the required emissions standards. The U.S. Environmental Protection Agency (EPA) has issued revised procedures for testing various engine categories. This common set of test requirements is set forth in 40 CFR part 1065 and is intended to streamline laboratory efforts, beginning in 2007, for both the EPA and industry and provide a basis for internationally harmonized test procedures for nearly all categories of engines.

The laboratory testing procedures set forth in part 1065 determine brake-specific emissions for duty-cycle testing using an engine dynamometer. This typically consists of one or more test intervals, each defined by a duty cycle, which is a sequence of speeds and torques that an engine must follow. The EPA is also adopting a requirement that manufacturers of heavy-duty highway engines use ramped-modal testing to show that they meet steady-state emission standards using the Supplemental Emissions Test (SET). Much like the part 1065 procedures, ramped-modal testing becomes mandatory in the 2010 model year. Ramped-modal testing involves a single, continuous emission measurement as the engine operates over the test modes in a defined sequence, including short transition segments between modes.

Regardless of the specific test procedure, it is imperative that the various constituent components of the exhaust gas be accurately collected and measured. Particulate matter (PM) is typically collected on a new fine-mesh filter that has been tare-weighted and loaded into a clean filter cartridge. The loaded cartridge is then placed in a test fixture connected to at least a representative portion of the exhaust gas stream produced by the test engine. During the test, PM is collected on the filter during engine operation over a specified duty cycle. The filter is then removed from the test fixture and weighted. The difference between the initial tare weight and the after-test weight is the mass of the collected particulate matter.

Heretofore, the test fixtures used to house a filter cartridge during a test have been containers, such as clamshell or hinged holders that are loaded and moved to a test chamber where they were connected, or plumbed, into all or a predefined portion of the engine exhaust gas stream. These fixtures were cumbersome to use and time consuming to connect. Typically, the exhaust gas flowing through the test fixture is diluted with air to reduce the flow stream temperature. Prior to a test, the test fixture is heated to a prescribed elevated test temperature, for example 47° C., and maintained at that temperature throughout the test. Accordingly, the individual installing or removing the filter cartridge had to use extreme caution, or use special handling tools to prevent burn injuries. The use of gloves when handling a test cartridge is discouraged because of potential contamination of the sample media.

The present invention is directed to overcoming the problems associated with loading, housing and removing filters used a sample collection media in particulate matter engine emission testing. It is desirable to have a test fixture for collecting particulate matter that can be preinstalled as an integral component of a laboratory testing system. It is also desirable to have such a test system that has a sealable filter containment chamber that is readily accessible for installing, sealing, and removing a sample collection filter without connection or disconnection with a laboratory testing system. Moreover, there is a need for a test fixture for collecting particulate matter discharged in the exhaust gas from an engine that does not require extensive cooling time or the use of special handling equipment to remove the test fixture or the filter collection media after a test.

SUMMARY OF THE INVENTION

In accordance with one aspect of the present invention, a test fixture for collecting particulate material has a first mounting plate that is disposed in transverse relationship with a predefined longitudinal axis of the test fixture. The first mounting plate has an opening through the plate that is adapted to receive a filter cartridge holder. The test fixture also includes a second mounting plate that is also transversely positioned with respect to longitudinal axis and is axially moveable along the axis between a first position spaced from the first mounting plate and a second position close to the first mounting plate. The second mounting plate also has an opening through the plate that is adapted to receive a filter cartridge holder. The test fixture also has a third mounting plate disposed in transverse relationship with the longitudinal axis and in fixed coaxial relationship with the first mounting plate. In addition, the test fixture embodying the present invention has a plurality of guide rods disposed in parallel radially spaced relationship with the longitudinal axis. Each of the guide rods has a first end attached to the first mounting plate and a second end attached to the third mounting plate.

Other features of the test fixture for collecting particulate material in accordance with the present invention include a first cartridge holder mounted in the opening in the first mounting plate and a second cartridge holder mounted in the opening in the second mounting plate. Each of the filter cartridge holders have a recess adapted to receive a respective portion of a filter cartridge and maintain the filter cartridge in a sealed transverse position with respect to the longitudinal axis when the second mounting plate is moved to the second position.

BRIEF DESCRIPTION OF THE DRAWINGS

A more complete understanding of the test fixture for collecting particulate material carried in the exhaust gas of an engine may be had by reference to the following detailed description when taken in conjunction with the accompanying drawings, wherein.

DETAILED DESCRIPTION OF THE INVENTION

Figure 1:
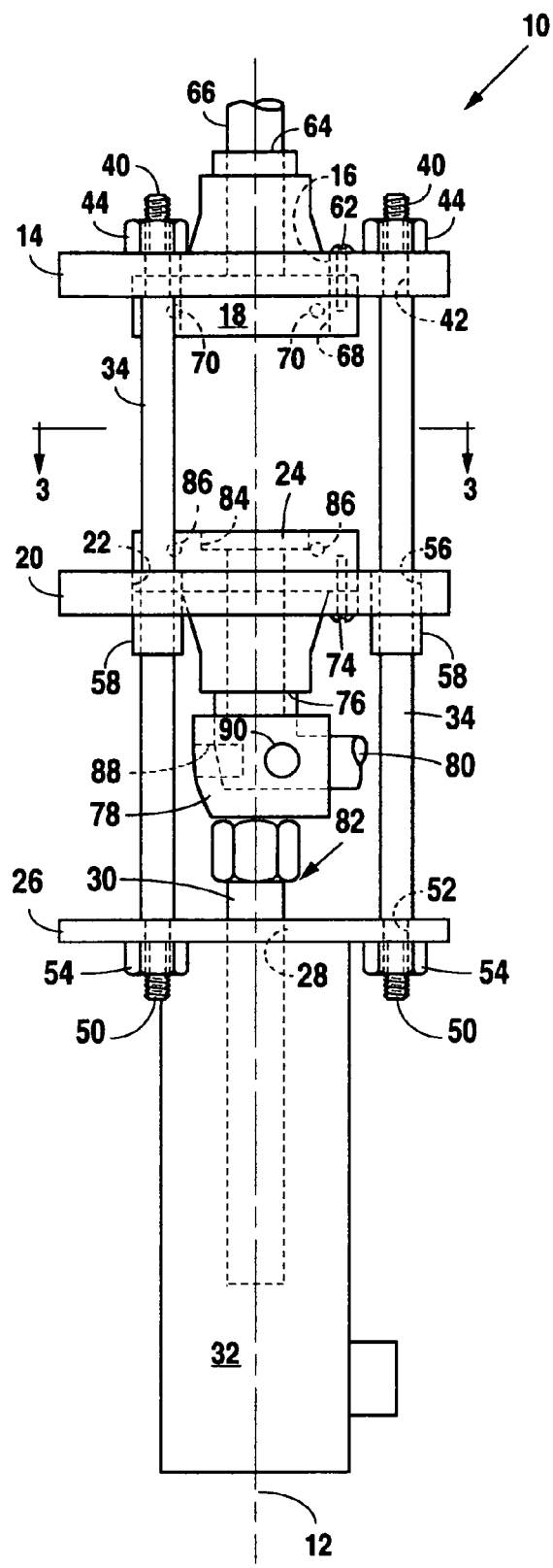
FIG. 1 is an elevation view showing the test fixture embodying the present invention in a first, or open, position.
Figure 2:
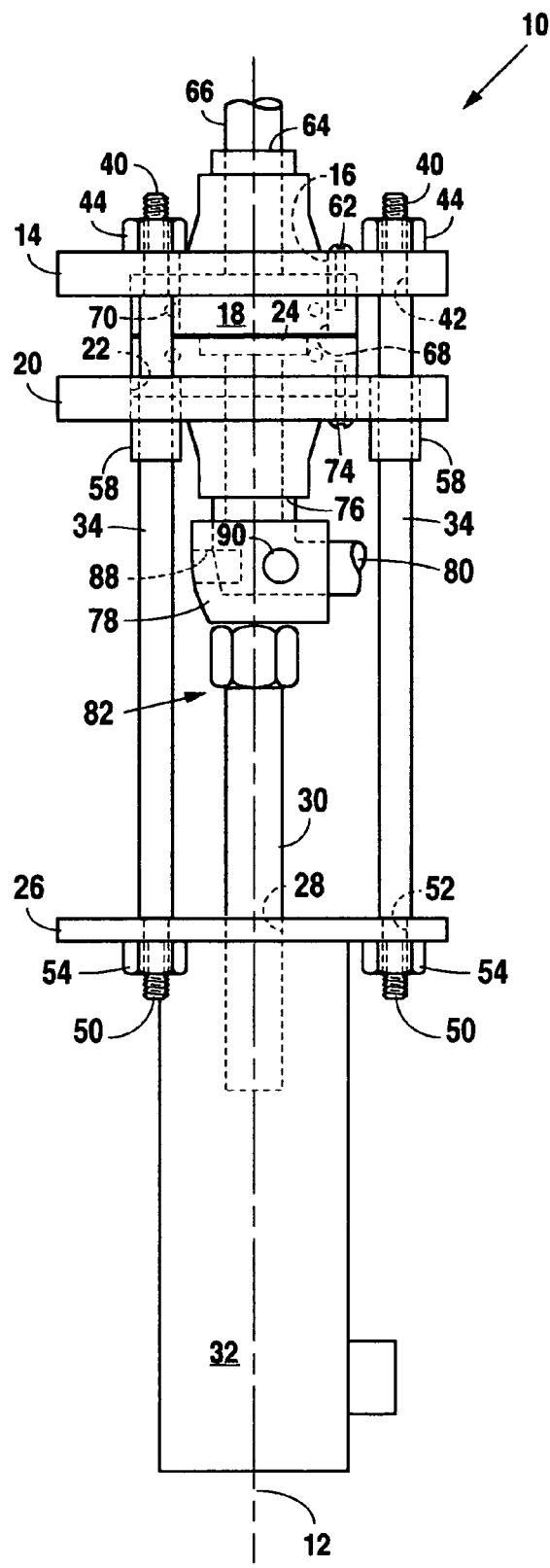
FIG. 2 is an elevation view showing the test fixture embodying the present invention in a second, or closed, position.
Figure 3:
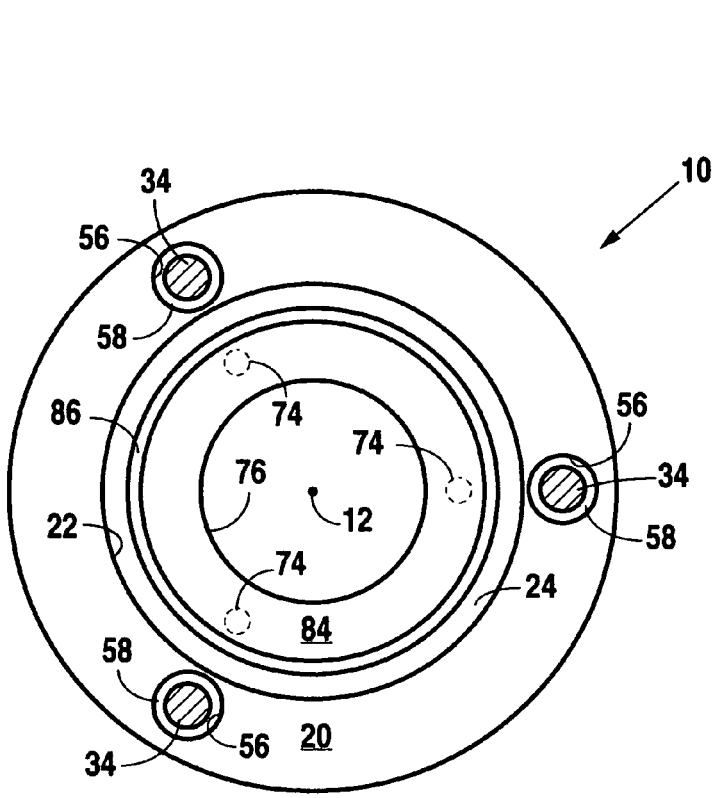
FIG. 3 is a cross-sectional view of the test fixture embodying the present invention, taken along the line 3-3 of FIG. 1; and, FIG. 4 is an elevation view of a guide rod component of the test fixture embodying the present invention.

A preferred embodiment of the test fixture for collecting particulate material in accordance with the present invention is generally indicated by the reference numeral 10 in FIGS. 1-3. The test fixture 10 has a predefined longitudinal axis 12 with three mounting plates disposed in transverse relationship with the longitudinal axis. A first mounting plate 14 has an opening 16 extending through the plate that is adapted to receive a first filter cartridge holder 18.

A second mounting plate 20, is also transversely disposed with respect to the longitudinal axis 12 and is axially movable with respect to the first mounting plate 14 along the longitudinal axis between a first, or open, position spaced from the first mounting plate as illustrated in FIG. 1 and a second, or closed position, in close proximity to the first mounting plate as shown in FIG. 2. The second mounting plate 20 has an opening 22 extending through the plate that is adapted to receive a second filter cartridge holder 24.

A third mounting plate 26 is also transversely positioned with respect to the longitudinal axis 12 and has an opening 28 through which an actuator rod 30 extends. The actuator rod 30 has a distal end mechanically connected to the second mounting plate 20 and is moved in an axial direction along the longitudinal axis 12 by a linear actuator 32 mounted on the third mounting plate 26. In the preferred embodiment of the present invention, the linear actuator 32 is a pneumatic cylinder controllably connected to a source of compressed air, not shown. Alternatively, the actuator 32 may be a hydraulic cylinder, an electrically powered ball-screw or rack and pinion actuator, or similar device.

Figure 4:
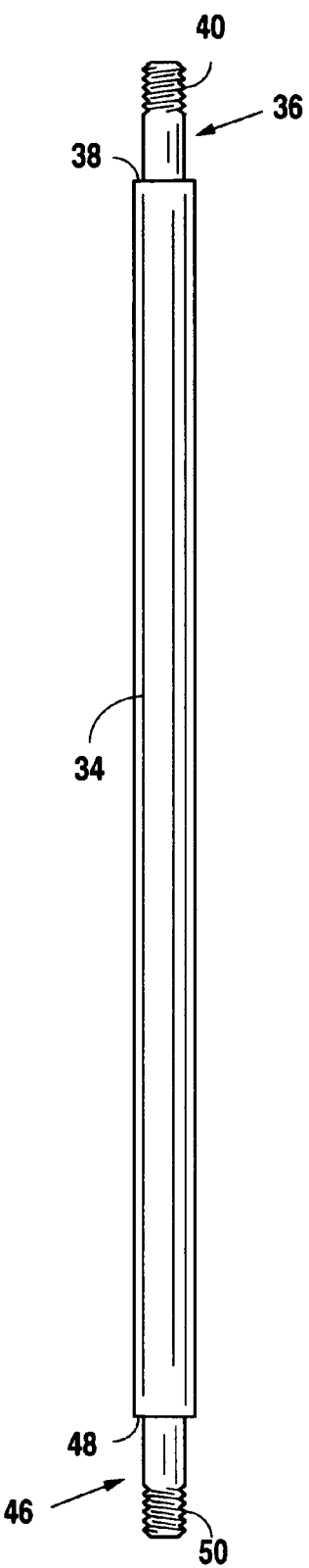

The test fixture 10 embodying the present invention also has a plurality of guide rods 34 disposed in parallel radially spaced relationship with respect to the longitudinal axis 12. As shown in greater detail in FIG. 4, each of the guide rods 34 has a stepped, reduced-diameter, first end 36 that provides a plate abutment shoulder 38 and has a distal treaded portion 40. In the preferred embodiment of the present invention, the first mounting plate 14 has three equally-distanced radially and circumferentially spaced apart bores 42 adapted to snugly receive the first end 36 of a respective guide rod 34. When assembled with the first mounting plate 14, the shoulders 38 of the respective guide rods 34 abut the first mounting plate and the guide rods secured in a fixed position with the mounting plate by nuts 44 threaded onto the distal threaded portions 40. In a similar manner, each of the guide rods 34 has a stepped, reduced-diameter, second end 46 that provides a plate abutment shoulder 48 and has a distal treaded portion 50. In the preferred embodiment of the present invention, the third mounting plate 26 has three equally-distanced radially and circumferentially spaced apart bores 52 adapted to snugly receive the second end 46 of a respective guide rod 34. When assembled with the third mounting plate 26, the shoulders 48 of the respective guide rods 34 abut the third mounting plate and are secured in a fixed position with the mounting plate by nuts 54 threaded onto the distal threaded portion 40.

The second mounting plate 20 has three equally-distanced radially and circumferentially spaced apart bores 56 each adapted to snugly receive a guide rod bushing 58. Preferably, the bushings are oil-impregnated permanently-lubricated sleeve bushings having an internal diameter sufficient to slideably receive and firmly support a respective guide rod 34 and thereby support the second mounting plate 20 in a manner that allows the plate to be moved axially with respect to the first mounting plate 14 along the longitudinal axis 12. Importantly, the guide rods 34 also maintain the second mounting plate 20 in coaxial alignment with first mounting plate 14 during movement of the second mounting plate between a first, or open, position illustrated in FIG. 1 and a second, or closed, position illustrated by FIG. 2.

The first filter cartridge holder 18 is removably mounted in the opening 16 provided in the first mounting plate 14 by a plurality of screws 62. The first cartridge holder 18 has an inlet port 64 connected to a conduit 66 that is in fluid communication with the exhaust gas produced by an engine being tested. The first filter cartridge holder 18 also has a recess 68 adapted to receive a respective portion of a filter cartridge, not shown, and maintain the filter cartridge is a transverse position with respect to longitudinal axis 12 of the test fixture 10. Standardized filter cartridges for collecting particular matter carried in an engine exhaust gas stream, also known as filter cassettes, are commercially available and typically consist of a fine-mesh glass fiber screen mounted in a polycarbonate ring. The size, i.e., diameter of the screen mounted in the filter cartridge ring is dependent upon specific test requirements such as the amount of exhaust gas produced and the relative portion of the exhaust gas stream sampled. In an illustrative embodiment, the diameter of the sample media, i.e., the collection screen, is 47 mm. An elastomeric O-ring 70 is retained in a circumferential groove provided in the recess 68 in the first filter cartridge holder 18 and provides a gas-tight seal between the holder and the mounting ring of the filter cartridge when the test fixture 10 is closed.

In a similar manner, the second filter cartridge holder 24 is removably mounted in the opening 22 provided in the second mounting plate 20 by a plurality of screws 74. The second cartridge holder 24 has an exhaust port 76 that is connected to an elbow fitting 78 that diverts the discharge exhaust gas flow 90 degrees to a flexible, or limitedly movable, exhaust discharge conduit 80. The elbow fitting 78 is attached to a distal end 82 of the actuator rod 30 and moves the second mounting plate 20 in an axial direction in response to movement of the actuator rod by the actuator 32. The second cartridge holder 24 also has a recess 84 adapted to receive another portion of the filter cartridge. An elastomeric O-ring 86 is retained in a circumferential groove provided in the recess 84 in the second filter cartridge holder 24 and provides a gas-tight seal between the holder and the mounting ring of the filter cartridge when the test fixture 10 is closed.

As an aid to test monitoring and data collection requirements, a pressure sensor may be installed in the exhaust gas conduit 66 and in a port 88 provided in the elbow fitting 78 to measure the pressure drop across the filter media as particulate matter accumulates on the media during a test. Exhaust gas temperature can also be measured by a thermocouple conveniently mounted in a temperature measurement port 90 provided in the elbow fitting 78. A typical test system may also include other sensing devices to measure oxides of nitrogen ($NO_x$), hydrocarbons (HC) carbon monoxide (CO) and/or other exhaust emissions. In addition, a vacuum pump connected with the exhaust discharge conduit 80 may be used to assist exhaust gas flow through the test system.

In operation, a new filter is tare-weighted and placed in a clean filter cartridge. Initially, the test fixture 10 is in the open position illustrated in FIG. 1, and the filter cartridge is easily inserted in the recess 84 provided in the second filter cartridge holder 24 attached to the second mounting plate 20. The actuator 32 is then operated to extend the actuator rod 30 and move the second mounting plate 20 along the longitudinal axis 12 of the test fixture, in a direction toward the first mounting plate 14, for a distance sufficient to bring the second filter cartridge holder 24 into contact with the first filter cartridge holder 18, i.e., to the closed position illustrated in FIG. 2. The test is then operated over a prescribed duty cycle and time period. During the test, the O-rings 70, 86 respectively disposed in the first filter cartridge holder 18 and the second filter cartridge holder 24 cooperate with the mounting ring of the enclosed filter cartridge to provide a sealed flow path for exhaust gas flowing through the test fixture 10. After the test is completed, the second mounting plate 20 is moved in an axial direction, either manually or by retraction of the actuator rod 30, away from the first mounting plate 14 to the initial open position. The filter cartridge containing the filter and collected particulate matter is removed from the recess, the filter removed from the mounting ring, and the filter containing particulate matter collected during the test is weighed. The initial tare-weight of the new filter is subtracted from the combined weight of the filter and collected particulate matter to determine the mass of the collected particulate matter.

From the above description, it can be seen that test fixture 10, embodying the present invention is particularly suited for incorporation as a fixed component in an exhaust gas test system. The test fixture 10 does not require time consuming and often difficult connection to an exhaust test system after loading a test cartridge. Moreover, after a test sequence, the filter media can be easily removed from the test fixture 10 without requiring lengthy cool-down time or special handling equipment.

Although the present invention is described in terms of a preferred embodiment, those skilled in the art will recognize that the construction of certain components of the test fixture 10 may be modified. For example, the filter cartridge holders 18, 24, maybe constructed so that the respective exhaust inlet and discharge ports 64, 80 are separately formed components and subsequently attached to a separately formed filter retaining component to provide the filter holders described herein. Such arrangements of the test fixture embodying the present invention are intended to fall within the scope of the following claims.

Other aspects, features, and advantages of the present invention may be obtained from a study of this disclosure and the drawings, along with the appended claims.

What we claim is:

1. A test fixture for collecting particulate material, said fixture having a predefined longitudinal axis and comprising:
    a first mounting plate disposed in transverse relationship with respect to said longitudinal axis of the fixture and having an opening extending through the plate, said opening being adapted to receive a portion of a filter cartridge holder therein;
    a second mounting plate disposed in transverse relationship with respect to said longitudinal axis of the fixture and axially moveable along said longitudinal axis between a first position spaced from said first mounting plate and a second position in proximate relationship with said first mounting plate, said second mounting plate having an opening extending through the plate, said opening being adapted to receive a portion of a filter cartridge holder therein;
    a third mounting plate disposed in transverse relationship with respect to said longitudinal axis of the fixture in fixed axial relationship with said first mounting plate and adapted to support an actuator having an extendable rod connected to said second mounting plate, said second mounting plate being operable between said first and said second positions in response to moving said extendable rod of the actuator while maintaining said first and third mounting plates in fixed axial relationship with each other; and
    a plurality of guide rods disposed in parallel radially spaced relationship with respect to said longitudinal axis of the fixture, each of said guide rods having a first end fixedly attached to said first mounting plate and a second end fixedly attached to said third mounting plating plate and having an external surface adapted to slideably support said second mounting plate.

2. The test fixture for collecting particulate material, as set forth in claim 1, wherein said fixture includes a first filter cartridge holder mounted in said opening extending through the first mounting plate and a second filter cartridge holder mounted in said opening extending through the second mounting plate.

3. The test fixture for collecting particulate material, as set forth in claim 2, wherein said first and second filter cartridge holders each have a recess adapted to receive a respective portion of a filter cartridge and maintain said filter cartridge in a sealed fixed transverse position with respect to the longitudinal axis of said fixture in response to axially moving said second mounting plate from said first to said second position.

4. The test fixture for collecting particulate material, as set forth in claim 3, wherein said first and second filter cartridge holders are maintained in abutting relationship with each other when said second mounting plate is at said second position.

5. The test fixture for collecting particulate material, as set forth in claim 1, wherein said second mounting plate has a plurality of radially spaced bores extending through the plate, each of said bores having a bushing secured therein adapted to slideably receive a respective one of said guide rods.

6. The test fixture for collecting particulate material, as set forth in claim 5, wherein said plurality of bores extending through the second mounting plate comprises three radially spaced bores disposed circumferentially equidistantly apart and said plurality of guide rods comprise three guide rods each slideably received within a bushing secured in a respective one of said bores in the second mounting plate.

* * * * *